(12) United States Patent
Brill (10) Patent No.: US 6,334,328 B1
(45) Date of Patent: Jan. 1, 2002

(54) SANITARY ICE MAKING AND DISPENSING APPARATUS

(75) Inventor: Frank D. Brill, Fox Lake, IL (US)

(73) Assignee: IMI Cornelius Inc., Anoka, MN (US)

( * ) Notice: Subject to any disclaimer, the term of this patent is extended or adjusted under 35 U.S.C. 154(b) by 0 days.

(21) Appl. No.: 09/520,390

(22) Filed: Mar. 8, 2000

Related U.S. Application Data (60) Provisional application No. 60/124,058, filed on Mar. 12, 1999.

(51) Int. Cl.[7] ............................................. F25D 17/02
(52) U.S. Cl. ................................................ 62/347; 62/78
(58) Field of Search ............................. 62/74, 78, 374; 210/192, 748; 422/24, 28, 37, 292

(56) References Cited

U.S. PATENT DOCUMENTS

| | | | | |
|---|---|---|---|---|
| 5,005,364 A | * | 4/1991 | Nelson | 62/76 |
| 5,184,633 A | * | 2/1993 | Langford | 422/292 |
| 5,430,228 A | * | 7/1995 | Ciambrone et al. | 210/760 |
| 5,458,851 A | * | 10/1995 | Schroeder et al. | 422/28 |
| 5,586,439 A | * | 12/1996 | Schlosser et al. | 62/78 |
| 5,709,799 A | * | 1/1998 | Enelhard | 210/748 |

* cited by examiner

*Primary Examiner*—William E. Tapolcal
*Assistant Examiner*—Mohammad M. Ali
(74) *Attorney, Agent, or Firm*—Sten Erik Hakanson

(57) ABSTRACT

The present invention is an apparatus and method for providing effective ozonation of water used in ice making equipment for the production of ice cubes and for the ozonation of ice retaining bins located within an ice/beverage dispenser for sanitizing and retarding the growth of microorganisms therein and in the drains associated therewith.

13 Claims, 7 Drawing Sheets

SANITARY ICE MAKING AND DISPENSING APPARATUS

This application claims benefit to Provisional Application 60/124,058 filed Mar. 12, 1999.

FIELD OF THE INVENTION

The present invention relates generally to methods and apparatus for maintaining a sanitary condition in an ice maker and beverage dispenser, and in particular to such methods and apparatus using ozone as a sanitizing agent.

BACKGROUND OF THE INVENTION

The need to keep ice making and dispensing and beverage dispensing equipment clean over time is well known in the art. It is understood that such equipment can become contaminated with microorganisms, such as, bacteria, yeast, fungi, and mold. Thus, for example, the ice forming evaporator, fluid lines and ice storage area found in such equipment must be periodically cleaned. In the case of beverage dispensers, overflow beverage can promote the growth of microorganisms resulting in the clogging of the drains thereof.

Manual cleaning with detergents and sterilizing chemicals can be effective, however, cleaning schedules are not, as a practical matter, always adhered to. In addition, the job may not be done satisfactorily in terms of a thorough cleaning and rinsing of the food contact and drain elements or tubes. Thus, systems have been developed including electronic controls that, in the case of an ice maker, automatically enter the machine into a sanitizing cycle wherein cleaning agents are pumped there through and subsequently rinsed off. Of course, the automatic systems can fail as well, where, for example, the cleaning agent reservoir runs out of cleaner, or the apparatus simply breaks down or fails to operate properly. Moreover, cleaning of the drains thereof is not specifically addressed or provided for in the prior art.

The use of ozone ($O_3$) as a sanitizing/oxidizing agent is well known, and especially its use to kill microorganisms in water. In ice machines, ozone has been used wherein a venturi is placed in the water line that runs from the water pump to the water distribution manifold. An ozone generator is connected to the venturi injector so that $O_3$ can be entrained into the water as it flows there through. Thus, $O_3$ is carried by the water over the ice making evaporator for providing some bactericidal or bacteriostatic effect. However, there is a need to provide for an ice maker and/or beverage dispenser wherein the ozone generator is an integral part thereof and where the produced ozone can be utilized more effectively so as to maintain a sufficient bacteriostatic condition. Furthermore, the is a need in the prior art to provide for such equipment having an extended life with respect to the ozone generator and to be resistant to any oxidation resulting from the presence of ozone in and around such equipment.

SUMMARY OF THE INVENTION

The present invention is an apparatus and method for providing effective ozonation of water used in ice making equipment for the production of ice cubes and for the ozonation of ice retaining bins for sanitizing and retarding the growth of micro-organisms therein and in the drains of beverage dispensing equipment.

In one embodiment of the present invention, a combination ice/beverage dispensing machine has an ice maker secured to a top end of a beverage dispenser. The ice maker produces ice that is dropped into and fills an ice retaining bin within the beverage machine. This type of combination is well known in the art and eliminates the need for manual loading of ice into the beverage dispensing machine.

As is also known, an ice maker typically includes a refrigeration component section and an ice making section separated by a dividing panel. The refrigeration component section includes a compressor, a condenser and fan and the associated electronics used for the operation thereof. An ice cube forming evaporator is located in the ice making section and includes a water distribution tube and a water receiving tank. As is known in the art, the ice maker as above described, includes a water pump that operates to pump water from a source thereof to the water distribution tube. The water then cascades over the surface of the evaporator. As the evaporator is cooled by operation of the refrigeration components, some of the water flowing there over will freeze thereon. The remainder of the water will flow into the receiving tank to be recycled by the pump to flow repeatedly over the evaporator until ice of a sufficient thickness is formed thereon. The ice is then harvested, typically by hot gas defrosting of the evaporator, causing the ice to melt slightly and slip off the evaporator and drop into the ice retaining bin of the beverage dispenser.

As is further understood, the beverage machine includes a plurality of beverage dispensing valves secured along a front surface thereof and includes a drip tray there below. An ice-dispensing chute typically extends from the same front surface and located centrally of the beverage valves. An ice delivering mechanism provides for transfer of ice from the ice retaining bin into the chute, which mechanism is activated when a cup, to be filled with ice, is placed below an open end of the ice chute. Any spillage of ice or beverage is caught by the drip tray and directed down a drain tube connected thereto. The ice bin includes a cold plate for receiving ice from the ice retaining bin for providing heat exchange cooling of the fluid beverage components flowing through individual tubes retained within the cold plate.

A merchandising structure is also secured to the front surface of the ice/beverage dispenser at a level thereon above that of the beverage valves. The merchandising structure includes a frame having a merchandising window to which various advertising transparencies can be secured. The transparencies are generally illuminated by means of back lighting thereof wherein a fluorescent bulb is secured to the ice/beverage dispenser front surface behind the transparency. The merchandising structure can be removed to reveal an interior panel. The panel is secured by means of a pivot hinge to the dispenser front surface and includes thereon-electrical sockets for engaging and retaining the fluorescent bulb. The panel can be swung down and open to reveal a component retaining area. An ozone generating device is secured within this component area. An appropriate electrical power supply circuit is retained in the component area and provides the correct power level necessary to operate the ozone generator. The ozone generator includes an air inlet and an air outlet. As is well understood regarding ozone generation in general, oxygen ($O_2$.) travels into the inlet so that the high electrical potential of the interior of the generator can result in the production of ozone ($O_3$) from the ambient air. The $O_3$ then travels out of the generator outlet. In the present invention, an air pump is secured to the inlet of the ozone generator. The outlet is secured to a tube running to the air inlet of a venturi. The venturi is located in the ice making machine in the refrigeration component section, and includes a water inlet and a water outlet. The venturi is fluidly connected in the stream of water running from the pump to the ice maker distribution tube. Thus, the water line running from the outlet of the pump is secured to the inlet of the venturi and the outlet of the venturi is secured to a tube extending to the water distribution tube.

In operation, the air pump provides a driving force for the $O_3$ produced by the ozone generator to flow into the air inlet of the venturi. During the time that ice is being produced, the water pump causes a flow of water through the venturi. Thus, the suction force produced by the venturi effect coupled with the driving force provided by the air pump was found to finely entrain very minute bubbles of the now $O_3$ rich air into the water. This $O_3$ rich water then flows into the water distribution tube over the evaporator. It was found that by enriching the $O_3$ content of the water in this manner using an air pump to provide for such improved mixing thereof, rather than rely on the inherent suction effect of the venturi alone, that sufficient quantities of $O_3$ would reach the water distribution tube, the evaporator and the receiving tank such that growth of microorganisms thereon was greatly reduced or eliminated.

In the above described embodiment a T-fitting can be used wherein a portion of the ozone produced by the generator is directed to a tube that ends at a fitting secured to a top edge of the ice retaining bin of the beverage dispenser. Thus, $O_3$ laden air is moved by the air pump up to and out of the ice bin fitting. As $O_3$ molecules are heavier than air, they fall under the force of gravity into the bin. It was found that the microorganism content of the bin and the water drain tube and growth thereon or therein was greatly reduced or eliminated. It was also discovered that such content and growth in the drip tray and associated drain tube was reduced or eliminated. In particular, the clogging type of growth in the drain tubes was not found to re-occur.

In the above described embodiment it was found that the bacteriostatic or bactericidal effects of the ozone were maximized in a method of operation wherein the ozone generator and the air pump ran continuously regardless if the ice maker was in an ice making mode or not. When not in the ice making state, i.e. when the water pump was not operating, the $O_3$ laden air did not mix with the water as well, however it would flow from the venturi in a reverse direction through the water pump into the receiving tank. At the same time it would flow in the "normal" direction from the venturi and up to the water distribution tube. Of course, a larger amount of $O_3$ would, during non ice making times, also flow into the ice retaining bin, as less would be demanded due to the absence of the suction effect of the venturi. When long ice maker off periods are encountered, a modification can be made to allow the water pump and venturi (along with the generator and air pump that are already energized) to operate when the unit is not making ice. This will permit continued circulation of $O_3$ containing water over the evaporator as if the ice maker were in an ice making mode.

In a second embodiment of the present invention, an ice maker and ice/beverage combination as above described is used, except no venturi is utilized and ozone is moved by the air pump only. In this further embodiment a tube runs directly from the outlet of the ozone generator to a fitting which enters into the water distribution tube that is located at the top perimeter edge of the ice making compartment. In this embodiment the $O_3$ laden air is more "passively" mixed with the ice making water, than in the first embodiment where a venturi is utilized. However, by using the strategy of also running the ozone generator continuously, it was found that a direct connection to the distribution tube also served to provide for a substantial reduction in microorganisms present or growing on or in the water distribution tube, the evaporator, the receiving tank and the pump and associated tubing. This embodiment was also found to reduce or eliminate the presence of microorganisms in the ice retaining bin and associated drain tubing, as well as in the ice dispensing chute, cold plate drains, drip tray and drain tube thereof.

In a third embodiment of the present invention, a beverage machine as above described is used, except no ice machine is secured to the top thereof. In this embodiment an ozone generator and air pump are used to feed a line running to a fitting secured to the top perimeter edge of the ice dispensing hopper. This embodiment was also found to reduce or eliminate the presence of microorganisms in the ice retaining bin and associated drain tube as well as in the ice dispensing chute, drip tray and drain tube thereof.

In a fourth embodiment, a drop in type beverage dispenser has an integral ozone generating system located in the tower portion thereof. The ozone is distributed to the ice bin and drip tray portions thereof for providing a germicidal effect therein.

DESCRIPTION OF THE DRAWINGS

A further understanding of the structure, function, operation, and objects and advantages of the present invention can be had by referring to the following detailed description that refers to the following figures, wherein.

DETAILED DESCRIPTION OF THE PREFERRED EMBODIMENTS

Figures 1, 2:
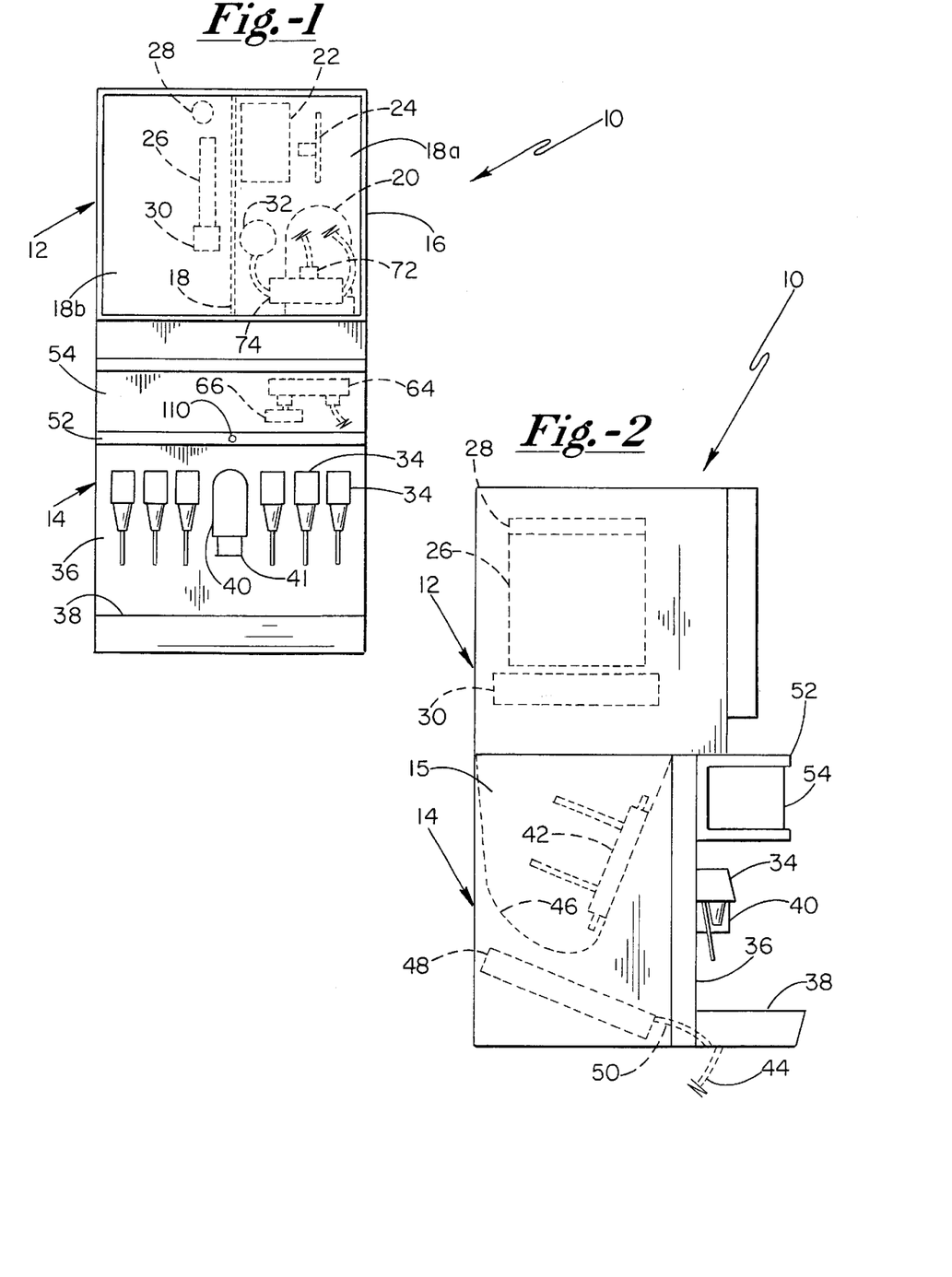
FIG. 1 shows a schematic front plan view of a combination ice maker and ice/beverage dispenser.
FIG. 2 shows a schematic side plan view of the dispenser of FIG. 2.

As seen by referring to FIGS. 1 and 2, a first embodiment of the present invention includes a combination ice/beverage dispensing machine 10 having an ice maker 12 secured to a top end of a beverage dispenser 14. Ice maker 12 produces particulate ice, such as cubes, that are dropped into an ice retaining bin 15 within beverage machine 14. This type of combination 10 is well known in the art and eliminates the need for manual loading of ice into a beverage machine.

As is also known, ice maker 12 typically includes a housing 16 defining an interior thereof that is divided by a plate 18 into a refrigeration component section 18a and an ice making section 18b. Refrigeration component section 18a includes a compressor 20, a condenser 22, a condenser fan 24, and the associated electronics used for the operation thereof, not shown. An ice cube forming evaporator 26 is located in ice making section 18b and includes a water distribution tube or manifold 28 extending along a top end thereof and includes a water receiving tank 30 extending along and beneath a bottom end thereof. As is known in the art, ice maker 12 includes a water pump 32 in refrigeration section 18a that operates to pump water from a source thereof and from tank 30 to water distribution tube 28. The water then cascades over the surface of evaporator 26 after exiting a plurality of holes extending through and along the length of tube 28. As is well understood, evaporator 26 is cooled by operation of the refrigeration compressor 20, a condenser 22 and fan 24, so that some of the water flowing there over will freeze thereon. The remainder of the water will flow into receiving tank 30 to be recycled by pump 32 to flow repeatedly over evaporator 26 until ice of a sufficient thickness is formed thereon. The ice cubes so formed are then harvested and dropped into ice retaining bin 15 of dispenser 14.

As is further understood, dispenser 14 includes a plurality of beverage dispensing valves 34 secured along a front surface 36 thereof and a drip tray 38 there below. An ice dispensing chute 40 typically extends from the same front surface 36 and extends therefrom in between valves 34. An ice delivering mechanism 42 provides for transfer or lifting of ice from ice retaining bin 14 into an opening, not shown, that leads into chute 40. As is known, a lever 41 operates a switch for operating mechanism 42 and also opening a door between chute 40 and bin 15 for permitting dispensing of ice into a cup when the cup is pressed against lever 41. Any spillage of ice or beverage is caught by drip tray 38 and directed down a drain tube 44 connected thereto. Ice bin 15 also includes an opening 46 through which ice can fall onto a cold plate 48. As is known in the art, cold plate 48 provides for cooling of the beverage liquid components that flow through serpentine coils therein to the valves 34. Melt water runs down the inclined cold plate 48 into a further drain tube 50 which also drains into driptray 38.

Figure 9:
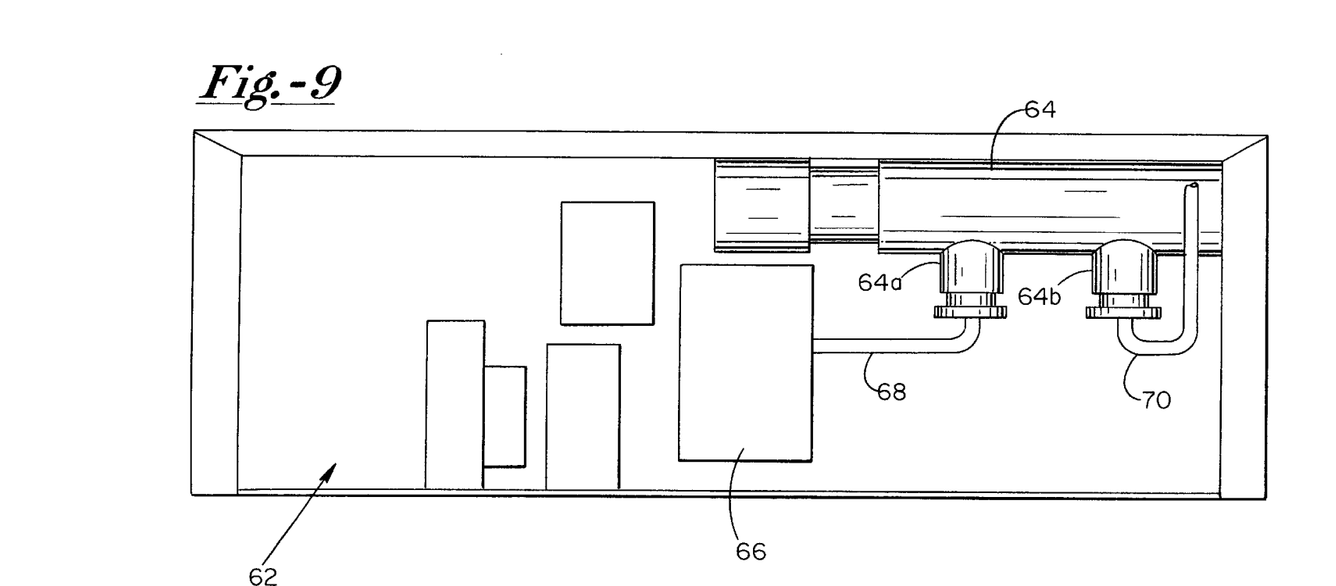
FIG. 9 invention shows an enlarged front plan view of the component area of the present invention.

A merchandising structure is also secured to front surface 36 of ice/beverage dispenser 10 at a level thereon above that of beverage valves 34. The merchandising structure includes a removable frame 52 that extends around and supports a merchandising window 54 to which various product indicating transparencies can be secured on an inner side thereof. The transparencies are generally illuminated by means of back lighting thereof wherein a fluorescent bulb is secured to ice/beverage dispenser front surface behind the transparency. As understood by also referring to FIGS. 7 and 9, a panel 58 is hingedly secured to dispenser front surface 36 and includes thereon electrical sockets 60 for engaging and retaining the fluorescent bulb. After removal of frame 52, panel 58 can be swung down to reveal a component retaining area 62. An ozone generating device 64 is secured within this component area, and an appropriate electrical power supply circuit is retained in the component area and to provide the correct power level necessary to operate ozone generator 64.

Figure 3:
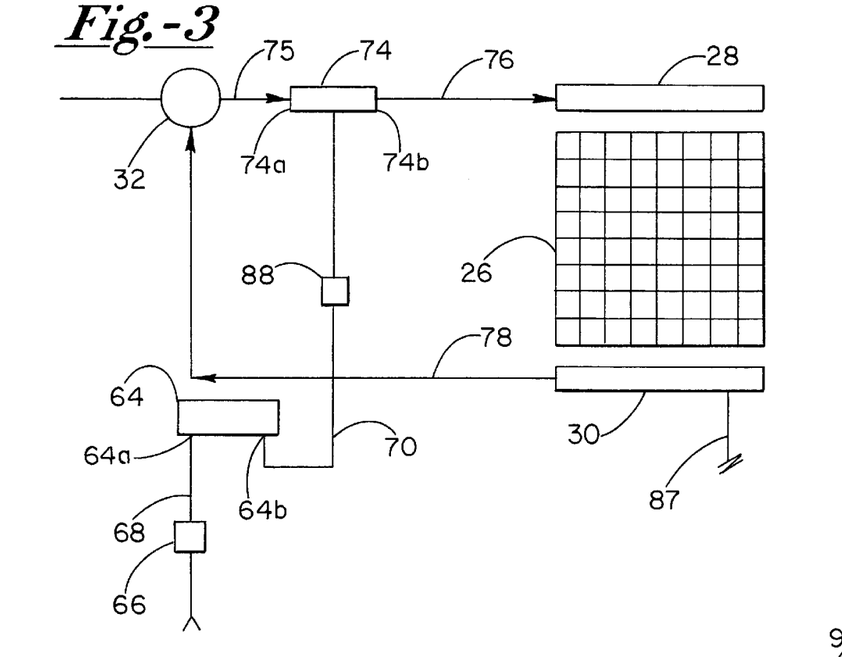
FIG. 3 shows a schematic representation of a first embodiment of the present invention.
Figure 10:
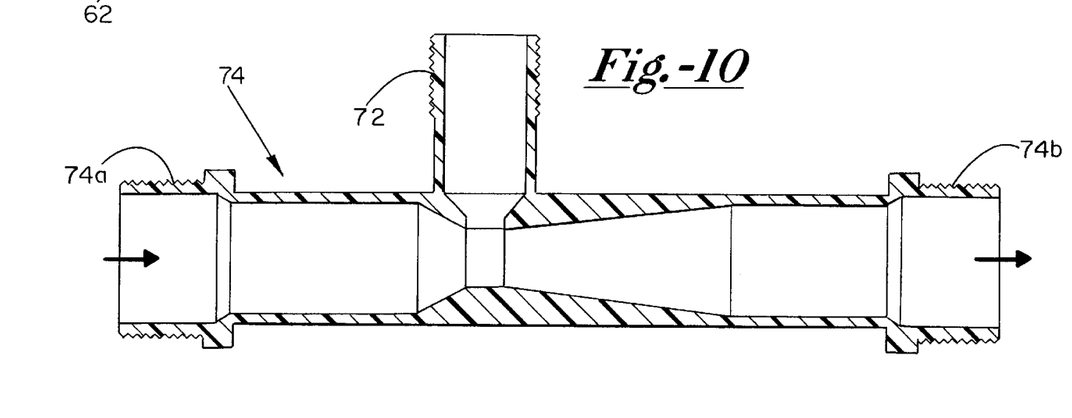
FIG. 10 shows an enlarged cross-sectional view of a venturi used in the present.

A seen by also referring to FIG. 3, ozone generator 64 includes an air inlet 64a and an air outlet 64b. As is well understood regarding ozone generation in general, ambient air travels into inlet 64a so that the high electrical potential of the interior of generator 64 can result in the production of ozone $O_3$ from the ambient oxygen $O_2$ therein. The $O_3$ enriched air then travels out of outlet 64b. In the present invention, an air pump 66, also secured in area 62, is fluidly connected by a tube 68 to inlet 64a. As seen by also referring to FIGS. 3 and 10, outlet 64b is secured to a tube 70 running to an air inlet 72 of a venturi 74. Venturi 74 is located in ice making machine 12 in refrigeration component section 18a, and includes a water inlet 74a and a water outlet 74b. Venturi inlet 74a is fluidly connected by a tube 75 to an outlet of pump 32 and outlet 74b is fluidly connected by a tube 76 to distribution tube 28. Pump 32 is fluidly connected to a line 78 extending to receiving tank 30. A float valve, not shown, in receiving tank 30 is connected by a line 87 to a source of potable water such as a pressurized municipal water supply. A check valve 88 prevents the reverse flow of water to generator 64.

In operation, air pump 66 provides a driving force for the $O_3$ produced by ozone generator 64 to flow into air inlet 72 of the venturi 74. During the time that ice is being produced, water pump 32 causes a flow of water through venturi 74. Thus, the suction force produced by the venturi effect coupled with the driving force provided by pump 66 was found to finely entrain very minute bubbles of the now $O_3$ rich air into the water to a greater extent than either of the two used separately. It was also found that $O_3$ was better entrained into the water where venturi 74 was oriented in a horizontal position. This $O_3$ rich water then flows into water distribution tube 28 and over the evaporator 26. It was found that by enriching the $O_3$ content of the water in this manner using air pump 66 to provide for such improved mixing thereof, rather than rely on the inherent suction effect of venturi 74 alone, that sufficient quantities of $O_3$ would reach water distribution tube 28, evaporator 26 and receiving tank 30 such that growth of microorganisms thereon was greatly reduced or eliminated.

The spraying and cascading of water over evaporator 26 releases some of the ozone entrained therein. As $O_3$ molecules are heavier than the than the $O_2$ and nitrogen ($N_2$) forming the primary components of the ambient air, the $O_3$ falls under the force of gravity into bin 15. It was found that the microorganism count or level of contamination of bin 15, cold plate 48 and drain tube 50 was greatly lowered or eliminated relative to non ozone treated equipment. It was also discovered that such content and growth in drip tray 38 and associated drain tube 44 was reduced or eliminated. In particular, the clogging type if growth that can become present in drain tubes 44 and 50 was not found to develop.

When not in the ice making state, i.e. when water pump 32, and the refrigeration system as well, are not operating, the $O_3$ laden air does not mix with the water as well as the venturi 74 can not create a suction. However, with air pump 66 running it will flow from venturi 74 in a reverse direction through water pump 32 into receiving tank 30. At the same time it will flow in the "normal" direction from venturi 74 and up to water distribution tube 28. Of course, a larger amount of $O_3$ will flow, during such non ice making times, into ice retaining bin 14, as less would be demanded due to the absence of the suction effect of venturi 74. In the above described embodiment it was found that the bacteriostatic or bactericidal effects of the ozone were maximized in a method of operation wherein ozone generator 64 and air pump 66 ran continuously, regardless if ice maker 12 was in an ice making mode or not. Ordinarily, when the ice maker is off, the water in the tank 30 is stagnant and growth of microorganisms can be accelerated thereby. That result is due to the fact that refrigeration and water pumping are both shut off when the ice bin is sensed as full of ice. An enhancement of the bacteriostatic or bactericidal effects is accomplished by energizing the water pump and ozonating and cycling the water over evaporator 26 even if bin 15 is sensed as full and the refrigeration components of ice maker 12 are shut off. Thus, the control of the present invention provides for such pump operation even during non-ice making times. However, water must not be permitted to spray from the evaporator into the ice bin below. In ice makers of the type having a curtain that extends closely parallel with the evaporator, it is necessary that it be in the closed position before water cycling over the evaporator occurs. Typically, such ice makers include a switch that indicates if the curtain is closed so that running of the pump 32 can be keyed thereto. For example, a further switch, not shown, can be added to the curtain to indicate a closed condition. This further switch can be used to operate a separate relay that provides power to water circulating pump 32 separately from the refrigeration compressor. Those of skill will understand that the ozone generator 64 and air pump 66 are continuously energized.

Figure 4:
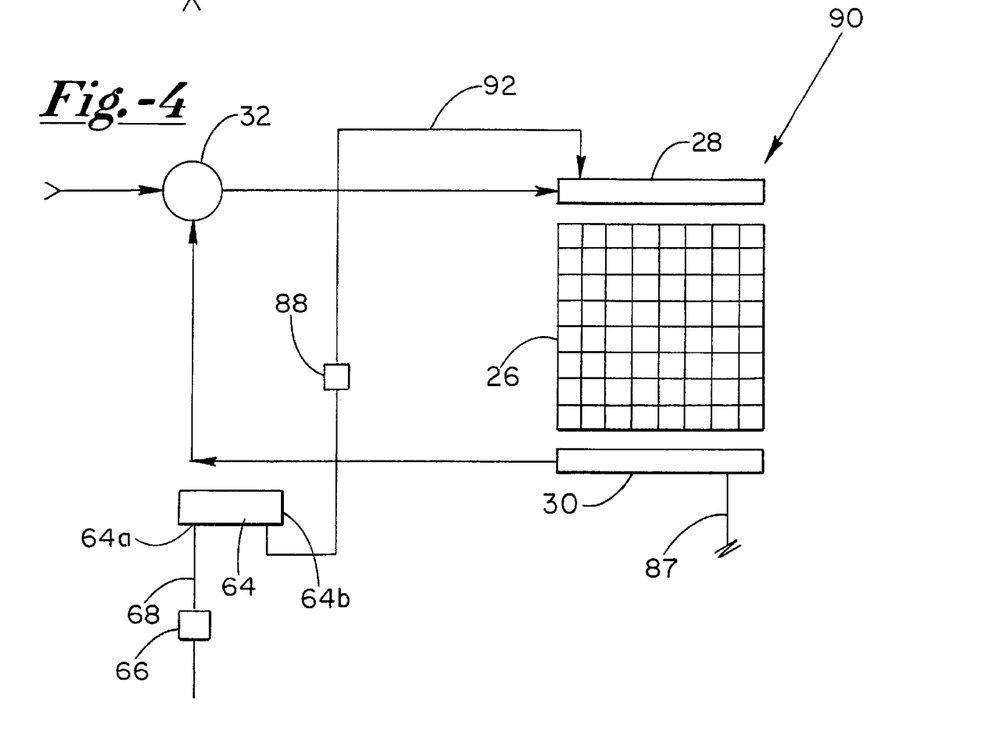
FIG. 4 shows a schematic representation of a second embodiment of the present invention.
Figure 5:
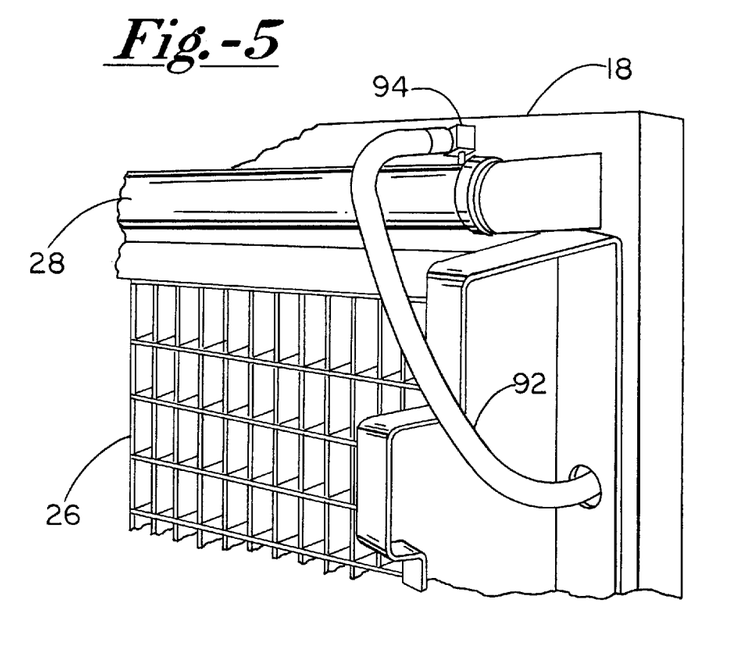
FIG. 5 shows an enlarged view of water distribution tube and associated evaporator.

As seen by referring to FIGS. 4 and 5, a second embodiment 90 of the present invention utilizing ice maker 12 and ice/beverage dispenser 10 is illustrated. As seen specifically in the schematic of FIG. 4, no venturi 74 is used. Instead a line 92 runs directly to distribution tube 28. As seen in FIG. 5, tube 92 is connected to a fitting 94 secured to tube 28. A check valve 88 in line 92 serves to prevent flow of water there through back to generator 64.

In the operation of embodiment 90, the $O_3$ laden air is more passively mixed with the ice making water than in the first embodiment where a venturi is utilized. However, by using the strategy of also running ozone generator 64 continuously, it was found that a direct connection to distribution tube 28 served to provide for a substantial reduction in microorganisms present or growing on or in tube 28, evaporator 26, and receiving tank 30, as well as with pump 32 and associated tubing.

Figure 6:
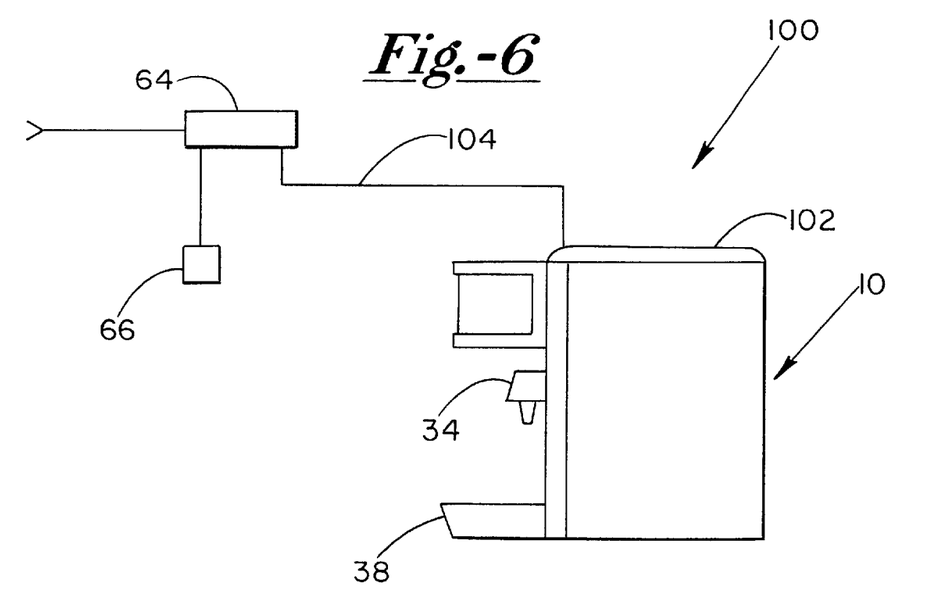
FIG. 6 shows a schematic representation of a third embodiment of the present invention.
Figure 7:
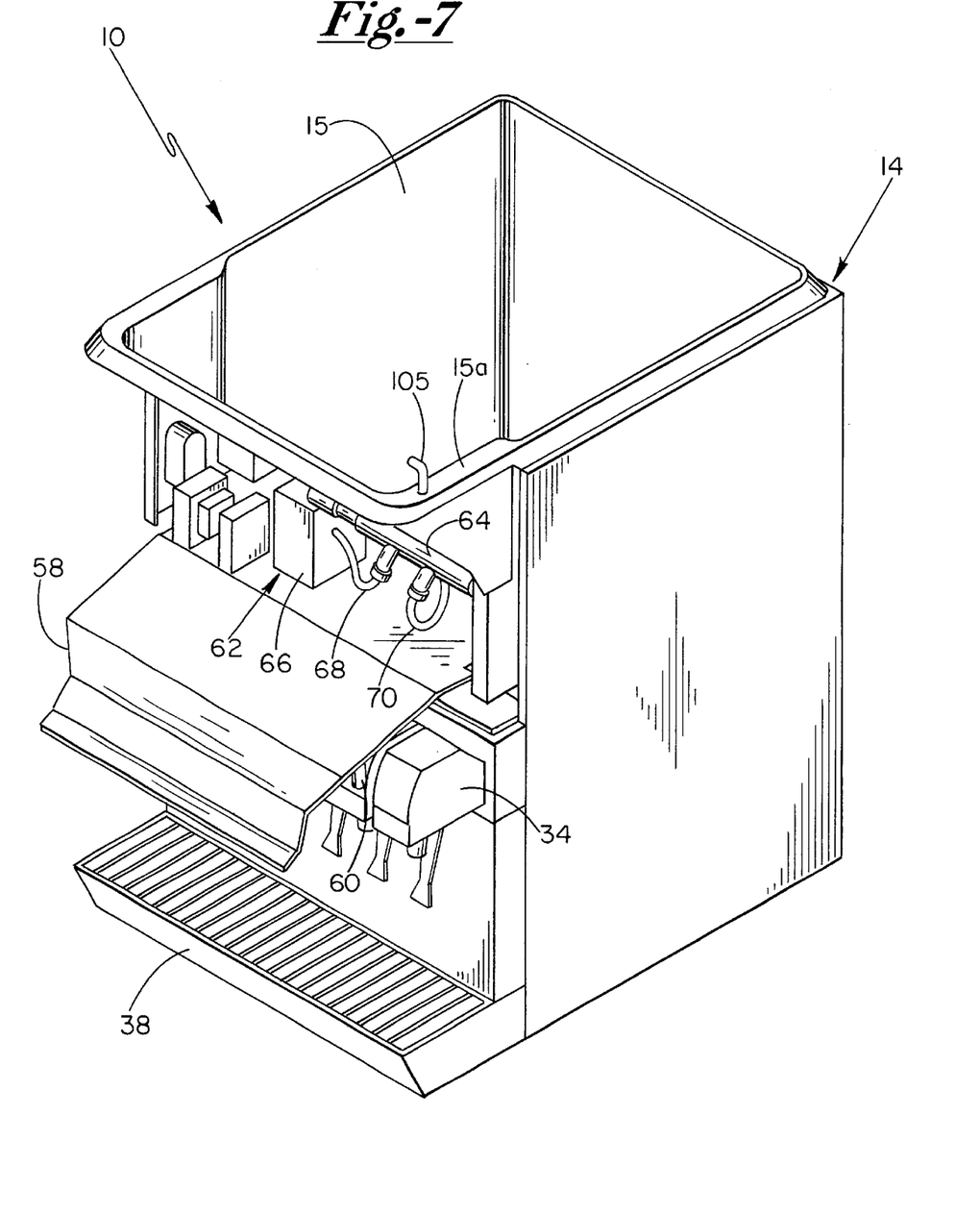
FIG. 7 shows a perspective view of an ice/beverage dispenser of the third embodiment of the present invention.

As seen by referring to FIGS. 6 and 7, a third embodiment 100 of the present invention is shown. In this embodiment no ice maker 12 is utilized wherein a full ice bin cover 102 serves to enclose cover ice bin area 15 in place of ice maker 12. In this embodiment ozone generator 64 is used only to feed a line 104 running to a fitting 105 secured to and extending from a top rim 15a of ice bin 15. Thus, embodiment 100 is only concerned with the delivery of ozone to ice bin 15. This embodiment was also found to reduce or eliminate the presence of microorganisms in ice retaining bin 15 and associated drain tube 48, as well as in ice dispensing chute 40, drip tray 38 and drain tube 50 thereof.

Figure 8:
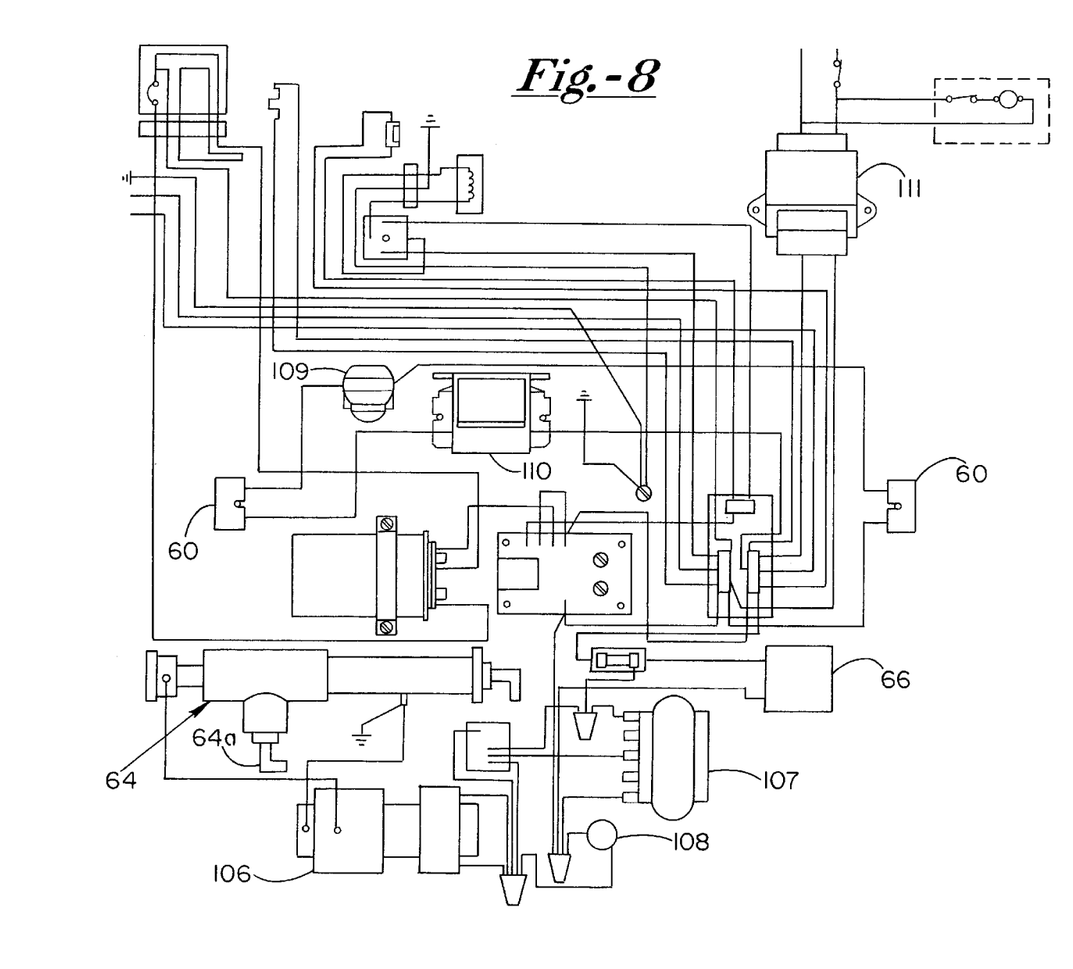
FIG. 8 shows an electrical and fluid schematic of the present invention.

An electrical schematic of the present invention is seen in FIG. 8. This schematic is essentially the same for various embodiments herein. A high voltage transformer 106 provides power to generator 64. A variable transformer 107 can be used to regulate the ozone output of generator 64. Thus, in situations where, for example, ice maker 12 is not operating to make ice, a lower $O_3$ output is acceptable. Therefore, the ice maker control can switch generator 64 to a lower output by means of adjusting the voltage output of transformer 107 down. Conversely, going into the ice making mode wherein pump 32 and compressor 20 are turned on will result in generator 64 being switched to a higher voltage. An indicator light 108 is secured to the exterior of merchandising frame 52 and serves to indicate when generator 64 is operating. Fluorescent light sockets 60 are powered by a starter 109 and a ballast 110. A transformer 111 provides power to valves 34.

In a particular reduction to practice of the present invention in accordance with the first embodiment described herein, bin 15 has a capacity of approximately 150 pounds, and ice maker 12 has an ice production capacity of 400 pounds per day. Generator 64 is manufactured by Ozotech Inc. of Yreka, Calif. and identified by model number 31249. This model of generator operates on 115 volt less and than ½ ampere of current and has an $O_3$ output of approximately 60 mg/hr. Venturi 74 is of the type manufactured by Mazzei Injector Corporation, of Bakersfield, Calif. and identified as model number 684K. The air pump is of the type manufactured by Second Nature of Blacksburg Virginia and identified as the Challenger II model having an air output of 1.2 liters/min. The lower voltage of 90 volts selected for the reduced output operation of generator 64 resulted in an output of 30 mg/hr.

Figure 11:
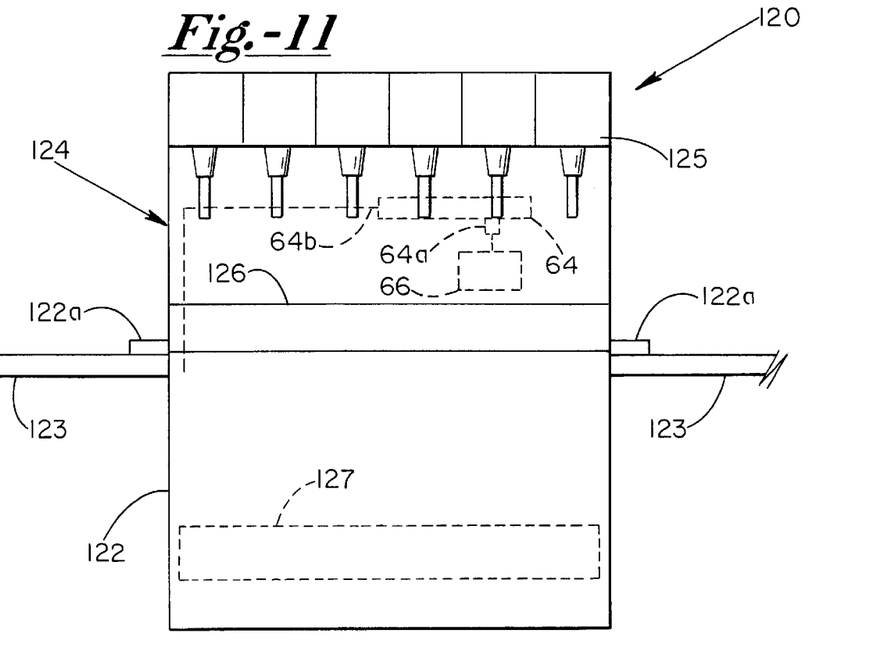
FIG. 11 shows a schematic representation of a front view of a fourth embodiment of the present invention.
Figure 12:
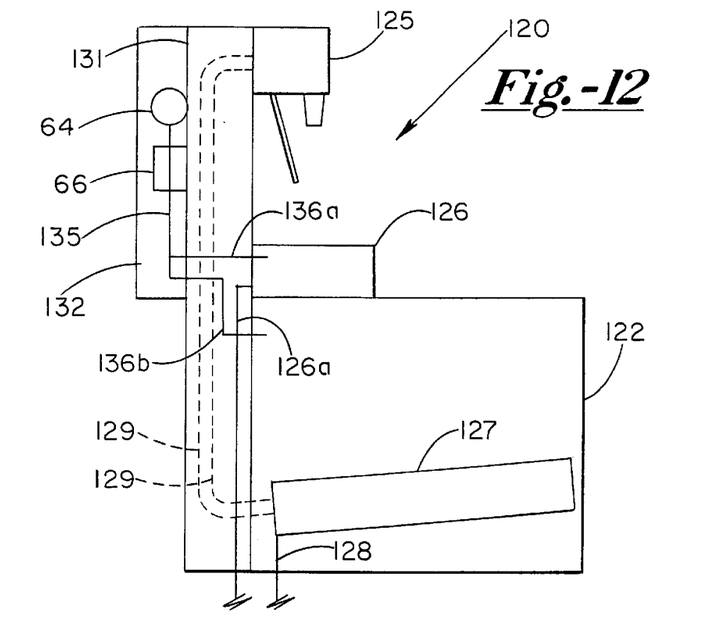
FIG. 12 shows a schematic representation of a side view of the fourth embodiment of the present invention.

As seen by referring to FIGS. 11 and 12, a further beverage embodiment of the present invention is shown. A dispenser 120 of the "drop in" type is shown. As is known, such dispensers include an ice bin 122 that is sized to drop into an appropriately sized hole in an existing counter top 123 and be supported in part by a perimeter flange 122a. A tower housing portion 124 extends there above and includes a plurality of valves 125 secured to an exterior top surface thereof. A drip tray and pan 126 is positioned below the valves 125 and includes a drain and drain line 126a. The bin 122 includes a cold plate 127, at the bottom thereof, generally positioned at an angle to allow melted ice to flow therefrom and out a drain and drain line 128. A plurality of beverage lines 129 extend from cold plate 127 up through housing 124 and connect to valves 125. A plate 131 is positioned within housing 124 and sealed around its perimeter for creating an interior space 132. Ozone generator 64 and air pump 66 are located within space 132 and can be secured to plate 131. Ozone is discharged into a tube system 135 having a tube 136a for directing a portion thereof into the beverage drip tray 126 and associated drain and drain line 126a. Ozone is also directed into a further tube portion 136b for moving a portion thereof into the ice storage bin 122 and cold plate 127 and its drain and drain line 128.

In operation, it can be appreciated that the ozone produced by generator 133 is delivered by pump 134 so that it falls into bin 122 and onto cold plate 127 and drain and drain line 128. Ozone is also delivered into drip tray and pan 126 and its drain and drain line 126a. A bacteriostatic effect is then provided for in both areas. It has been found that such an approach serves to greatly reduce the growth of microorganisms and the drain blocking associated therewith. Housing 124 can be understood to be somewhat expanded in horizontal width to accommodate generator 64 and pump 66 as well as the electronics associated therewith, not shown, within space 132. However, that additional width can be on the order of only three to four inches. Panel 132 provides for keeping ozone producing elements and electronics dry through isolation from lines 129 and ice bin 122. Ozone delivery tubes 136a and 136b can extend through panel 131 and be sealed around there circumference at the point of passage there through. Internal space 132 is vented to provide for a dry air source.

What is claimed is:

1. In an ice/beverage dispenser having an ice maker secured thereto for delivering ice into an ice retaining bin area of the ice/beverage dispenser, the improvement comprising:

an ozone generator secured to the ice/beverage dispenser and having an air inlet and an air outlet, an air pump connected to the air inlet of the ozone generator, a venturi having an air inlet, a water inlet and a water outlet, and the venturi air inlet in fluid communication with the air outlet of the ozone generator, and the venturi water inlet in fluid communication with a water pump pumping water thereto from a source thereof, and the water outlet of the venturi fluidly connected to a distribution tube of the ice maker.

2. A method of inhibiting the growth of microorganisms in an ice maker, the ice maker having mechanical refrigeration components including an ice making evaporator cooled by the operation of a compressor and condenser, the ice maker having an ice making cycle during which ice is formed on the evaporator by operation of the compressor and condenser, a harvest cycle during which ice is harvested from the evaporator and an off cycle when the compressor is not running and ice is not being formed on the evaporator, the method comprising the steps of:

Initiating a recirculating flow of water over the evaporator,

Entraining ozone into that circulating flow of water,

Maintaining said recirculating flow and entraining of ozone except during the harvest cycle.

3. An ice maker, comprising:

an ice forming evaporator cooled by the operation of a refrigeration system including a compressor and condenser, a water pump fluidly connected to a water recirculating system for providing a recirculating flow of water there through and over the evaporator for forming ice on the evaporator when it is cooled by operation of the refrigeration system, a venturi fluidly connected to the water recirculating system so that the recirculating water flows there through by action of the water pump, an ozone generator having an inlet fluidly connect to an air pump and an outlet fluidly connected to an air inlet of the venturi for entraining ozone produced by the ozone generator into the recirculating water as it flows through the venturi.

4. A method of operating an ice maker, the ice maker comprising, an ice forming evaporator cooled by the operation of a refrigeration system including a compressor and condenser, a water pump fluidly connected to a water recirculating system for providing a recirculating flow of water there through and over the evaporator for forming ice on the evaporator when it is cooled by operation of the refrigeration system, a venturi fluidly connected to the water recirculating system so that the recirculating water flows there through by action of the water pump, an ozone generator having an inlet fluidly connect to an air pump and an outlet fluidly connected to an air inlet of the venturi for entraining ozone produced by the ozone generator into the recirculating water as it flows through the venturi, the method of operating the ice maker comprising the steps of:

commencing an ice making cycle by cooling the evaporator and operating the water pump to commence the recirculating flow of water over the evaporator to form ice thereon, and operating the air pump and the ozone generator for entraining ozone into the recirculating flow of water.

5. The method as defined in claim 4, and further including the steps of:

turning off the water pump and the ozone generator, and subsequently harvesting the ice from the evaporator.

6. The method as defined in claim 5, and further including the steps of:

operating the water pump to commence the recirculating flow of water, and operating the air pump and the ozone generator for entraining ozone into the recirculating flow of water during an off period when the evaporator is not being cooled and when ice is not being harvested there from.

7. A combination ice maker and beverage dispenser, comprising:

and ice maker having an ice forming evaporator cooled by the operation of a refrigeration system including a compressor and condenser, a water pump fluidly connected to a water recirculating system for providing a recirculating flow of water there through and over the evaporator for forming ice on the evaporator when it is cooled by operation of the refrigeration system, a venturi fluidly connected to the water recirculating system so that the recirculating water flows there through by action of the water pump, a beverage dispenser having an ice retaining bin and having a front surface to which a plurality of beverage dispensing valves are secured along a first horizontal level thereof and the ice maker secured to a top end of the beverage dispenser so that ice made thereby can fall into the ice retaining bin, and an ozone generator having an inlet fluidly connect to an air pump and an outlet fluidly connected to an air inlet of the venturi for entraining ozone produced by the ozone generator into the recirculating water as it flows through the venturi.

8. The device as defined in claim 7, and the ozone generator located in a front access area of the beverage dispenser and interior of the front surface thereof.

9. The device as defined in claim 8, and the front access area of the beverage dispenser located at a second horizontal level above the first horizontal level.

10. A beverage dispenser, comprising:

an ice retaining bin and having a front surface to which a plurality of beverage dispensing valves are secured along a first horizontal level thereof, an ozone generator having an inlet fluidly connect to an air pump and an outlet fluidly connected to a tube terminating in or adjacent the ice retaining bin so that operation of the air pump and the ozone generator provide for introduction of ozone into the ice retaining bin.

11. The device as defined in claim 10, and the ozone generator and pump located in a front access area of the beverage dispenser and interior of the front surface thereof.

12. The device as defined in claim 11, and the front access area of the beverage dispenser located at a second horizontal level above the beverage valves at the first horizontal level.

13. A beverage dispenser, comprising:

an ice retaining bin having a bottom end and four sidewalls extending upward there from to a top perimeter edge and having a cold plate within the ice retaining bin and adjacent the bottom end thereof, a beverage valve tower secured to a back end portion of the ice retaining bin top perimeter edge and extending upward there from and having a plurality of beverage dispensing valves secured along a front surface thereof along a top end thereof, and the tower having an ozone generator having an inlet fluidly connect to an air pump and an outlet fluidly connected to a tube terminating in or adjacent the ice retaining bin so that operation of the air pump and the ozone generator provide for introduction of ozone into the ice retaining bin.

\* \* \* \* \*